United States Patent
Bosch et al.

(10) Patent No.: US 7,034,170 B2
(45) Date of Patent: Apr. 25, 2006

(54) MANGANESE(IV) COMPLEX SALTS AND THEIR USE AS OXIDATION CATALYSTS

(75) Inventors: Marco Bosch, Mannheim (DE); Dario Veghini, Brig (CH)

(73) Assignee: Lonza AG, Basel (CH)

( * ) Notice: Subject to any disclaimer, the term of this patent is extended or adjusted under 35 U.S.C. 154(b) by 10 days.

(21) Appl. No.: 10/501,471

(22) PCT Filed: Jan. 13, 2003

(86) PCT No.: PCT/EP03/00218

§ 371 (c)(1),
(2), (4) Date: Jul. 14, 2004

(87) PCT Pub. No.: WO03/059510

PCT Pub. Date: Jul. 24, 2003

(65) Prior Publication Data

US 2005/0065378 A1    Mar. 24, 2005

(30) Foreign Application Priority Data

Jan. 15, 2002 (EP) .................. 02000866

(51) Int. Cl.
C07F 19/00 (2006.01)
C07F 13/00 (2006.01)
B01J 31/00 (2006.01)
C07C 51/16 (2006.01)
C07C 45/00 (2006.01)

(52) U.S. Cl. .............................. 556/28; 556/9; 556/10; 556/14; 549/523; 568/402; 568/426; 568/471; 562/407; 562/519; 502/162

(58) Field of Classification Search .............. 556/9, 556/10, 14, 28; 502/162; 549/523; 562/519, 562/407; 568/402, 426, 471
See application file for complete search history.

(56) References Cited

U.S. PATENT DOCUMENTS 5,153,161 A * 10/1992 Kerschner et al. .......... 502/167
5,536,441 A * 7/1996 Chapple et al. ......... 252/186.33
5,968,881 A * 10/1999 Haeggberg et al. ......... 510/226

FOREIGN PATENT DOCUMENTS

EP  0458397   11/1991
JP  11286700  10/1999

OTHER PUBLICATIONS

Minoru Kishi et al., "Detergent Compositions for Removeal of Oily Soils in Kitchen", Chemical Abstracts Services. No. 131:273428.

Shul'pin, G.B. et al., "Oxidations by the System . . . ", Tetrahedron, Elsevier Science Publishers, vol. 55, No. 17 (Apr. 23, 1999), pp. 5345-5358.

Smith, J.R. Lindsay, et al., "Stereoselective Oxygenation of Alkanes by Peroxyacetic Acid or Hydrogen Peroxide and Acetic Acid Catalysed by a Manganese (IV) 1,4,7-triazacyclononane Complex", Tetrahedron Letters, Elsevier Science Publishers, vol. 39, No. 27 (Jul. 2, 1998, p 4909-4912).

Schuchardt, V., et al. "Cyclohexane Oxidation continue to be a challenge", Applied Catalysis A: Denerol, vol. 211 (2001), pp. 1-17.

* cited by examiner

Primary Examiner—Porfirio Nazario-Gonzalez
(74) Attorney, Agent, or Firm—Fisher, Christen & Sabol

(57) ABSTRACT

Manganese(IV) complex salts of formula $[LMn(\mu\text{-}O)_3MnL]_n$ $[XM_{12}O_{40}]_m$, (I), wherein L is 1,4,7-trimethyl-1,4,7-triazacyclononane, X is P or Si, M is Mo or W, n is 2 or 3, and m is 1 or 2, with the provisos that (i) if X is Si, then n=2 and m=1 and (ii) if X is P, then n=3 and m=2. These compounds are active catalysts in the partial oxidation of various organic compounds with peroxy compounds, e.g., the preparation of ketones from secondary alcohols or the epoxidation of olefins.

13 Claims, No Drawings

MANGANESE(IV) COMPLEX SALTS AND THEIR USE AS OXIDATION CATALYSTS

This application is a 371 national stage application of International (PCT) Application No. PCT/EP03/00218, filed on Jan. 13, 2004, that has priority benefit of European Patent Application No. 02000866.0, filed on Jan. 15, 2002.

The invention relates to novel manganese(IV) complexes and their application as oxidation catalysts in the partial oxidation of organic compounds using peroxy compounds as oxidants.

Certain manganese(IV) complex salts, in particular those comprising the dinuclear complex dication [LMn($\mu$-O)$_3$MnL]$^{2+}$ wherein L is the tridentate amine ligand 1,4,7-trimethyl-1,4,7-triazacyclononane and whose structure is

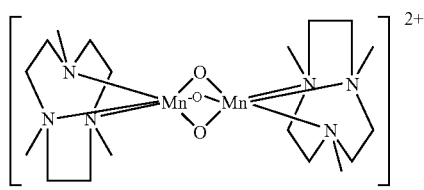

are known to be efficient oxidation catalysts (G. B. Shul'pin et al. *Tetrahedron* 1999, 55, 5345–5358; G. B. Shul'pin et al., *J. Mol. Catal. A: Chem.* 2001, 170, 17–34). They are usually employed as hexafluorophosphates which are soluble in polar organic solvents such as acetonitrile.

The solubility of these complexes is somewhat disadvantageous in that it impedes the work-up of the reaction mixtures after utilizing the complexes as oxidation catalysts and the reusability of the catalysts.

The problem to be solved by the instant invention was therefore to provide insoluble or sparingly soluble manganese(IV) complex salts having comparable or even improved catalytic activity.

According to the invention, this problem has been solved by the manganese(IV) heteropolymolybdates and tungstates of the formula $$[LMn(\mu\text{-}O)_3MnL]_n[XM_{12})O_{40}]_m \qquad (I),$$

wherein L is 1,4,7-trimethyl-1,4-7-triazacyclononane, X is P or Si, M is Mo or W, n is 2 or 3, and m is 1 or 2, with the provisos that (i) if X is Si, then n =2 and m =1 and
(ii) if X is P, then n =3 and m =2.

It has been found that these complex salts are virtually insoluble in all common solvents, and nevertheless their catalytic activity is comparable or even superior to that of the corresponding soluble hexafluorophosphate. Due to their insolublity, they can easily and completely be removed (e. g., by filtration, the residual Mn and M content of the filtrate being<10 ppm) from the reaction mixture after completion of the oxidation and may be reused several times without significant loss of activity. It is also possible to dilute the complex salts of the invention with suitable solid inert materials (e. g., silica) and use the thus obtained mixtures as catalysts in fixed-bed reactors (e. g., packed columns) for continuous or semi-continuous liquid-phase reactions.

The manganese(IV) complex salts of the invention may be easily prepared by reacting a solution of the above mentioned hexafluorophosphate of formula $$[LMn(\mu\text{-}O)_3MnL)](PF_6)_2,$$

wherein L is 1,4,7-trimethyl-1,4-7-triazacyclononane, with a heteropolyacid of formula $$H_oXM_{12}O_{40}$$

wherein X and M are as defined above, o=4 for X=Si and o=3 for X=P, and subsequently isolating the precipitated manganese(IV) heteropolyacid complex salt. The preparation is preferably carried out using acetonitrile as solvent for the hexafluorophosphate and water or a lower alcohol, in particular methanol or ethanol, or an aqueous lower alcohol as solvent for the heteropolyacid.

The manganese(IV) complex salts of the invention can be used as catalysts in the partial oxidation of organic compounds with peroxy compounds.

Preferred peroxy compounds are hydrogen peroxide, peroxycarboxylic acids and mixtures thereof. It should be noted that hydrogen peroxide reacts with carboxylic acids to give peroxycarboxylic acids in an equilibrium reaction. It is also possible to use other peroxy compounds, for example, tert-butyl hydroperoxide.

A preferred use of the manganese(IV) complex salts of the invention is their use as catalysts in a process for the production of aldehydes and/or carboxylic acids of formula $$R^1\text{—CHO} \qquad (II)$$

and/or $$R^1\text{—COOH} \qquad (III),$$

wherein $R^1$ is linear or branched $C_{1\text{-}10}$-alkyl, aryl or aryl-$C_{1\text{-}4}$-alkyl, which process comprises reacting an alcohol of formula $$R^1\text{—CH}_2\text{OH} \qquad (IV),$$

wherein $R^1$ is as defined above, with a peroxy compound. Depending on the reaction conditions and the residue $R^1$ the product is either an aldehyde or a carboxylic acid or a mixture thereof.

Linear or branched $C_{1\text{-}10}$-alkyl groups are here and hereinbelow, for example, methyl, ethyl, propyl, isopropyl, butyl, isobutyl, sec-butyl, tert-butyl, pentyl, 2-methylbutyl, 3-methylbutyl, 2,2-dimethylpropyl, hexyl, heptyl, octyl, nonyl and decyl, including all isomers of these groups.

Aryl groups are preferably phenyl or naphthyl, optionally substituted with one or more halogen atoms, $C_{1\text{-}10}$-alkyl or $C_{1\text{-}10}$-alkoxy groups.

Aryl-$C_{1\text{-}4}$-alkyl groups are $C_{1\text{-}4}$-alkyl groups substituted with the aryl groups defined above. In particular, aryl-$C_{1\text{-}4}$-alkyl groups are groups such as benzyl, 1-phenylethyl, 2-phenylethyl or 3-phenylpropyl.

Another preferred use of the manganese(IV) complex salts of the invention is their use as catalysts in a process for the production of ketones of formula $$R^2\text{—C(=O)—}R^3 \qquad (V),$$

wherein $R^2$ and $R^3$ are independently linear or branched $C_{1\text{-}10}$-alkyl, aryl or aryl-$C_{1\text{-}4}$-alkyl; or $R^2$ and $R^3$ together with the carbonyl group form a carbocyclic ring, which process comprises reacting an alcohol of formula $$R^2\text{—CHOH—}R^3 \qquad (VI),$$

wherein $R^2$ and $R^3$ are as defined above, with a peroxy compound. Ketones of formula (V) wherein $R^2$ and $R^3$ together with the carbonyl group form a carbocyclic ring are, for example, cyclic $C_{3-8}$-ketones such as cyclopropanone, cyclobutanone, cyclopentanone, cyclohexanone, cycloheptanone or cyclooctanone.

Still another preferred use of the manganese(IV) complex salts of the invention is their use as catalysts in a process for the production of 1,4-cyclohexanedione, which process comprises reacting 1,4-cyclohexanediol with a peroxy compound.

Still another preferred use of the manganese(IV) complex salts of the invention is their use as catalysts in a process for the production of oxiranes of formula

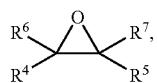

(VII)

wherein $R^4$, $R^5$, $R^6$ and $R^7$ are independently hydrogen, linear or branched $C_{1-10}$-alkyl, aryl or aryl-$C_{1-4}$-alkyl; or $R^4$ and $R^5$ together with the adjacent carbon atoms form a carbocyclic ring and $R^6$ and $R^7$ are as defined above, which process comprises reacting an olefin of formula

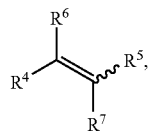

(VIII)

wherein $R^4$, $R^5$, $R^6$ and $R^7$ are as defined above for formula (VII), with a peroxy compound.

Olefins of formula (VIII) wherein $R^4$ and $R^5$ together with the adjacent carbon atoms form a carbocyclic ring are, for example, cyclopentene, cyclohexene or cycloheptene or the various terpene-derived cyclic olefins such as α-pinene.

Another preferred use of the manganese(IV) complex salts of the invention is their use as catalysts in a process for the oxidation of aliphatic, alicyclic or araliphatic hydrocarbons to the corresponding hydroxy or keto compounds, which process comprises reacting said hydrocarbons with a peroxy compound. Alicyclic hydrocarbons suitable for this process are, for example, cyclopentane or cyclohexane which may be oxidized to the corresponding cycloalkanols or cycloalkanones or mixtures thereof. Araliphatic hydrocarbons suitable for this process are, for example, diphenylmethane or tetrahydronaphthalene which may be oxidized to benzhydrol and benzophenone or 1,2,3,4-tetrahydro-1-naphthol and α-tetralone, respectively.

In a preferred embodiment of the above processes using the manganese(IV) complex salts of the invention, a $C_{2-6}$-alkanoic acid is used as an additive, acetic acid being especially preferred.

The following non-limiting examples illustrate the preparation of the manganese(IV) complex salts of the invention and their use as oxidation catalysts.

EXAMPLE 1

Synthesis of [LMn(μ-O)$_3$MnL](PF$_6$)$_2$

A mixture of 1.98 g (10 mmol) of MnCl$_2$.4H$_2$O, 1.93 ml (1.71 g, 10 mmol) of 1,4,7-trimethyl-1,4,7-triazacyclononane and 2.76 g (15 mmol) of potassium hexafluorophosphate in 60 ml of ethanol/water (2:1) was heated for 20 min at 50° C. and subsequently cooled to 0° C. To the resulting reaction mixture were added 10 ml (10 mmol) of 1 M aqueous hydrogen peroxide and 15 ml (15 mmol) of 1 M aqueous NaOH dropwise. During the addition the solution turned from brown to red. The mixture was then warmed up to room temperature, 2 M aqueous H$_2$SO$_4$ was dropwise added till a pH=8 was reached and then stirred 1 h at room temperature. The resulting solution was then filtered over Celite® and the filter cake washed 3 times with 20 ml of acetonitrile. The solution was then dried in vacuo (without heating). The residue was dissolved in 50 ml of acetonitrile and filtered over Celite®. The volume of the clear solution was then reduced to 20 ml. Slow addition of 120 ml of diethyl ether caused the precipitation of [LMn(μ-O)$_3$MnL](PF$_6$)$_2$ as a red-orange microcrystalline solid. Prolonged drying in vacuo gave 3.2 g of the title compound (81% of theory).

Elemental analysis: [LMn(μ-O)$_3$MnL](PF$_6$)$_2$ =C$_{18}$H$_{42}$F$_{12}$Mn$_2$N$_6$O$_3$P$_2$, 790.37 g/mol. Calcd.: C, 27.35; H, 5.36; N, 10.6. Found: C, 25.9; H, 5.1; N, 10.1.

EXAMPLE 2

Synthesis of [LMn(μ-O)$_3$MnL]$_2$[SiW$_{12}$O$_{40}$]

A solution of 1.37 g (1.73 mmol) of [LMn(μ-O)$_3$MnL](PF6)$_2$ in 20 ml of acetonitrile was added dropwise at room temperature to a solution of 2.80 g (0.97 mmol) of H$_4$SiW$_{12}$O$_{40}$.xH$_2$O in 20 ml of ethanol/water (2:1). This resulted in the formation of a dark-orange solid. After that, 60 ml of methanol were added and the suspension was stirred for 1 h. After filtration the light orange solid obtained was washed twice with 20 ml of water, 20 ml of methanol and 20 ml of diethyl ether. The resulting solid was dried 1.5 h in vacuo (125 mbar, 35° C.) to give 3.07 g of the title compound as a light orange solid (81% of theory).

Elemental analysis: [LMn(μ-O)$_3$MnL]$_2$[SiW$_{12}$O$_{40}$] =C$_{36}$H$_{84}$Mn$_4$N$_{12}$O$_{46}$SiW$_{12}$, 3875.02 g/mol. Water content=5.7%. Calcd.: C, 11.16; H, 2.18; N, 4.34. Calcd with 5.7% water: C, 10.55; H, 2.63; N, 4.10. Found: C, 8.7; H, 1.8; N, 3.4.

EXAMPLE 3

Synthesis of [LMn(μ-O)$_3$MnL]$_3$[PW$_{12}$O$_{40}$]$_2$

The preparation was analogous to the one described in the preceding example, using 0.79 g (1.00 mmol) of [LMn(μ-O)$_3$MnL](PF$_6$)$_2$ in 20 ml of acetonitrile and 2.88 g (1.00 mmol) of H$_3$PW$_{12}$O$_{40}$.xH$_2$O in 20 ml of methanol. After work up 2 g of the light orange product [LMn(μ-O)$_3$MnL]$_3$[PW$_{12}$O$_{40}$]$_2$ were obtained (83% of theory).

Elemental analysis: [LMn(μ-O)$_3$MnL]$_3$[PW$_{12}$O$_{40}$]$_2$ =C$_{54}$H$_{126}$Mn$_6$N$_{18}$O$_{89}$P$_2$W$_{24}$, 7255.38 g/mol Water content=1.9%. Calcd.: C, 11.16; H, 2.18; N, 4.34. Calcd. with 1.9% water: C, 8.94; H, 1.89; N, 3.47. Found: C, 8.8; H, 1.7; N, 3.4.

EXAMPLE 4

Synthesis of [LMn(μ-O)$_3$MnL]$_3$[PMo$_{12}$O$_{40}$]$_2$

The preparation was analogous to the one described in example 2, using 0.24 g (0.30 mmol) of [LMn(μ-O)$_3$MnL](PF$_6$)$_2$ in 20 ml of acetonitrile and 0.55 g (0.30 mmol) of H$_3$PMo$_{12}$O$_{40}$.xH$_2$O in 20 ml of methanol. After work up 0.54 g of the brown product [LMn(μ-O)$_3$MnL]$_3$[PMo$_{12}$O$_{40}$]$_2$ were obtained (83% of theory).

Elemental analysis: [LMn(μ-O)$_3$MnL]$_3$[PMo$_{12}$O$_{40}$]$_2$ =C$_{54}$H$_{126}$Mn$_6$N$_{18}$O$_{89}$P$_2$Mo$_{24}$, 5145.78 g/mol Water content=3.5%. Calcd.: C, 12.60; H, 2.47; N, 4.90. Calcd. with 3.5% water: C, 12.17; H, 2.74; N, 4.73. Found: C, 13.4; H, 2.4; N, 5.0.

EXAMPLES 5–15

Oxidation Reactions

General Procedure

In a 25 ml round bottom flask were introduced 9.24 mmol of substrate, 5 ml of acetonitrile, 0.014 mmol of acetic acid, 100 μl of chlorobenzene (internal standard) and 10 wt.-% of catalyst. Under vigourous stirring at 25° C., a solution of 130.8 mmol of hydrogen peroxide in 5 ml of acetonitrile was added within 15 to 30 minutes. Stirring was continued for 2 h at the same temperature.

EXAMPLES 5–10

Oxidation of Alcohols

EXAMPLE 5

Substrate: benzyl alcohol, 0.997 g
Catalyst: [LMn(μ-O)$_3$MnL]$_3$[PW$_{12}$O$_{40}$]$_2$, 0.100 g
Conversion: >98%
Yield: >98% benzoic acid.

EXAMPLE 6

Substrate: 1-hexanol, 0.943 g
Catalyst: [LMn(μ-O)$_3$MnL]$_3$[PW$_{12}$O$_{40}$]$_2$, 0.100 g
Conversion: 65%
Yield: 25% hexanal, 40% hexanoic acid

EXAMPLE 7

Substrate: 2-hexanol, 0.943 g
Catalyst: [LMn(μ-O)$_3$MnL]$_3$[PW$_{12}$O$_{40}$]$_2$, 0.100 g
Conversion: 100%
Yield: 80% 2-hexanone

EXAMPLE 8

Substrate: 2-octanol, 1.20 g
Catalyst: [LMn(μ-O)$_3$MnL]$_3$[PW$_{12}$O$_{40}$]$_2$, 0.100 g
Conversion: 55%
Yield: 45% 2-octanone

EXAMPLE 9

Substrate: cyclohexanol, 0.924 g
Catalyst: [LMn(μ-O)$_3$MnL]$_3$[PW$_{12}$O$_{40}$]$_2$, 0.100 g
Conversion: 80%
Yield: 80% cyclohexanone

EXAMPLE 10

Substrate: 1,4-cyclohekanediol, 1.072 g
Catalyst: [LMn(μ-O)$_3$MnL]$_2$[SiW$_{12}$O$_{40}$], 0.100 g
Conversion: 100%
Yield: >98% 1,4-cyclohexanedione The same catalyst was repeatedly used, whereby its activity decreased by less than 4% after 5 oxidation batches.

EXAMPLES 11–13

Epoxidation of Olefins

EXAMPLE 11

Substrate: cyclohexene, 0.758 g
Catalyst: [LMn(μ-O)$_3$MnL]$_2$[SiW$_{12}$O$_{40}$], 0.080 g
Conversion: >75%
Yield: >50% 7-oxabicyclo[4.1.0]heptane (cyclohexeneoxide)

EXAMPLE 12

Substrate: styrene, 0.962 g
Catalyst: [LMn(μ-O)$_3$MnL]$_2$[SiW$_{12}$O$_{40}$], 0.100 g
Conversion: 50%
Yield: 30% phenyloxirane

EXAMPLE 13

Substrate: 1-hexene, 0.776 g
Catalyst: [LMn(μ-O)$_3$MnL]$_2$[SiW$_{12}$O$_{40}$], 0.80 g
Conversion: 55%
Yield: 55% n-butyloxirane

EXAMPLES 14–15

Oxidation of Cycloalkanes

EXAMPLE 14

Substrate: cyclohexane, 0.776 g
Catalyst: [LMn(μ-O)$_3$MnL]$_2$[SiW$_{12}$O$_{40}$], 0.080 g
Conversion: >60%
Yield: >36% cyclohexanol, 8% cyclohexanone.

EXAMPLE 15

Substrate: 1,2,3,4-tetrahydronaphthalene, 1.220 g
Catalyst: [LMn(μ-O)$_3$MnL]$_2$[SiW$_{12}$O$_{40}$], 0.100 g
Conversion: 60%
Yield: 30% 1,2,3,4-tetrahydro-1-naphthol, 25% 3,4-dihydro-1(2H)-naphthalenone (α-tetralone).

The invention claim is:

1. Manganese(IV) complex salts of formula:

$$[LMn(\mu\text{-}O)_3MnL]_n[XM_{12}O_{40}]_m \quad (I),$$

wherein L is 1,4,7-trimethyl-1,4-7-triazacyclononane, X is P or Si, M is Mo or W, n is 2 or 3, and m is 1 or 2, with the provisos that
  (i) if X is Si, then n=2 and m=1 and
  (ii) if X is P, then n=3 and m=2.

2. A process for the production of the manganese(IV) complex salts of claim 1, which process comprises reacting a solution of the hexafluorophosphate of formula:

$$[LMn(\mu\text{-}O)_3MnL](PF_6)_2,$$

wherein L is as defined in claim 1, with a heteropolyacid of formula:

$$H_oXM_{12}O_{40}$$

wherein X and M are as defined in claim 1, o=4 for X=Si and o=3 for X=P, and subsequently isolating the precipitated manganese (IV) heteropolyacid complex salt.

3. The method of utilizing the manganese (IV) complex salts of claim 1 as catalysts in the partial oxidation of organic compounds with peroxy compounds.

4. A process for the production of aldehydes and/or carboxylic acids of formula $$R^1-CHO \quad (II)$$

and/or $$R^1-COOH \quad (III),$$

wherein $R^1$ is linear or branched $C_{1-10}$-alkyl, aryl or aryl-$C_{1-4}$-alkyl, comprising reacting an alcohol of formula $$R^1-CH_2OH \quad (IV),$$

wherein $R^1$ is as defined above, with a peroxy compound in the presence of a manganese (IV) complex salt of claim 1.

5. A process for the production of ketones of formula $$R^2-C(=O)-R^3 \quad (V),$$

wherein $R^2$ and $R^3$ are independently linear or branched $C_{1-10}$-alkyl, aryl or aryl-$C_{1-4}$-alkyl; or $R^2$ and $R^3$ together with the carbonyl group form a carbocyclic ring, comprising reacting an alcohol of formula $$R^2-CHOH-R^3 \quad (VI),$$

wherein $R^2$ and $R^3$ are as defined above, with a peroxy compound in the presence of a manganese(IV) complex salt of claim 1.

6. A process for the production of 1,4-cyclohexanedione, comprising reacting 1,4-cyclo-hexanediol with a peroxy compound in the presence of a manganese (IV) complex salt of claim 1.

7. A process for the production of oxiranes of formula

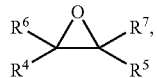
(VII)

wherein $R^4$, $R^5$, $R^6$ and $R^7$ are independently hydrogen, linear or branched $C_{1-10}$-alkyl, aryl or aryl-$C_{1-4}$-alkyl; or $R^4$ and $R^5$ together with the adjacent carbon atoms form a carbocyclic ring and $R^6$ and $R^7$ are as defined above, comprising reacting an olefin of formula

wherein $R^4$, $R^5$, $R^6$ and $R^7$ are as defined above for formula (VII), with a peroxy compound in the presence of a manganese(IV) complex salt of claim 1.

8. A process for the oxidation of aliphatic, alicyclic or araliphatic hydrocarbons to the corresponding hydroxy or keto compounds, comprising reacting said hydrocarbons with a peroxy compound in the presence of a manganese(IV) complex salt of claim 1.

9. The process of claim 4 wherein acetic acid is used as additive.

10. The process of claim 5 wherein acetic acid is used as additive.

11. The process of claim 6 wherein acetic acid is used as additive.

12. The process of claim 7 wherein acetic acid is used as additive.

13. The process of claim 8 wherein acetic acid is used as additive.

* * * * *